(12) United States Patent
Lee et al.

(10) Patent No.: US 11,395,734 B2
(45) Date of Patent: Jul. 26, 2022

(54) PROSTHETIC VALVE AND PROSTHETIC VALVE IMPLANTING METHOD

(71) Applicant: Shanghai Joy Medical Devices Co., Ltd., Shanghai (CN)

(72) Inventors: Shouyan Lee, Rancho Santa Margarita, CA (US); Hongxia Nan, Shanghai (CN)

(73) Assignee: SHANGHAI JOY MEDICAL DEVICES CO., LTD., Shanghai (CN)

( * ) Notice: Subject to any disclaimer, the term of this patent is extended or adjusted under 35 U.S.C. 154(b) by 512 days.

(21) Appl. No.: 16/333,148

(22) PCT Filed: Apr. 7, 2017

(86) PCT No.: PCT/CN2017/079778
§ 371 (c)(1),
(2) Date: Mar. 13, 2019

(87) PCT Pub. No.: WO2018/184226
PCT Pub. Date: Oct. 11, 2018

(65) Prior Publication Data
US 2019/0209304 A1    Jul. 11, 2019

(51) Int. Cl.
*A61F 2/24*    (2006.01)

(52) U.S. Cl.
CPC .......... *A61F 2/2418* (2013.01); *A61F 2/2475* (2013.01); *A61F 2/2415* (2013.01);
(Continued)

(58) Field of Classification Search
CPC ............ A61F 2/2418; A61F 2250/0082; A61F 2/24–2424; A61F 2/2475; A61F 2/82–945
See application file for complete search history.

(56) References Cited

U.S. PATENT DOCUMENTS

2004/0176839 A1*  9/2004  Huynh .................. A61F 2/2445
                                                              623/2.4
2004/0206363 A1   10/2004  McCartin
(Continued)

FOREIGN PATENT DOCUMENTS

WO        2005013854        2/2005

*Primary Examiner* — Rebecca S Preston
(74) *Attorney, Agent, or Firm* — Treasure IP Group, LLC

(57) ABSTRACT

A prosthetic valve, solving the technical problem of an existing prosthetic valve, when implanted in a certain valve site, not being adaptive to the physiological anatomy condition of the heart, being difficult to mount and fix properly and being easy to become displaced, and consequently affecting the function of the valve. The prosthetic valve comprises an annular frame (2) which has a mesh structure and can radially expand to deform; a connection line (10) is provided on the frame (2); the prosthetic valve is connected and fixed to an anatomical structure of a mounting position of a human body by means of the connection line (10); the connection line (10) surrounds the outside of the frame (2) to form several connection portions which extend out along the radial direction of the frame (2); the space surrounded by the connection portions can receive the thickness of the anatomical structure. The prosthetic valve is connected and fixed by means of the connection line (10) to an anatomical structure of a mounting position in a human body, e.g. a vessel wall, being mounted stably and being applicable to a patient on whom a valve replacement surgery is difficult to perform, e.g. a pulmonary artery stenosis patient.

14 Claims, 8 Drawing Sheets

(52) U.S. Cl.
CPC ..... *A61F 2/2442* (2013.01); *A61F 2220/0008* (2013.01); *A61F 2250/0069* (2013.01); *A61F 2250/0082* (2013.01)

(56) References Cited

U.S. PATENT DOCUMENTS

2004/0236356 A1* 11/2004 Rioux ................ A61B 17/0469
606/144
2014/0364943 A1* 12/2014 Conklin ................ A61F 2/2412
623/2.11

* cited by examiner

PROSTHETIC VALVE AND PROSTHETIC VALVE IMPLANTING METHOD

CROSS REFERENCE TO RELATED APPLICATION

This application is a national stage application of PCT/CN2017/079778, filed on Apr. 7, 2017. The international application is incorporated herein by reference in its entirety.

TECHNICAL FIELD

The present disclosure relates to a prosthetic valve, which can be implanted in the position of a pulmonary valve or other valve in a human body, and can replace the pulmonary valve or tricuspid valve damaged by a lesion. The present disclosure relates to a method for implanting a prosthetic valve.

BACKGROUND OF THE INVENTION

A human heart has four pumping chambers, that is, atrium sinistrum, atrium dextrum, ventriculus sinister and ventriculus dexter. The atriums receive blood from veins and pump it into the ventricles, and the ventricles discharge the blood to arteries. Atrium sinistrum, atrium dextrum, ventriculus sinister and ventriculus dexter individually have a valve, and the four valves control the blood stream that circulates through the human body. The mitral valve, located on the left part of heart, connects the atrium sinistrum with the ventriculus sinister, and the aortic valve connects the ventriculus sinister with the aorta. The two valves deliver oxygenated blood from the lungs into the aorta for distribution through the body. The tricuspid valve connecting the atrium dextrum and ventriculus dexter and the pulmonary valve connecting the ventriculus dexter and the pulmonary artery are located on the right part of heart, and together they deliver deoxygenated blood from the body to the lungs. The tricuspid valve is defined by fibrous rings of collagen, each of which is referred to as a valve annulus, and form part of the fiber skeleton of heart. The valve annulus provides peripheral attachment for the three cuspides or leaflets of tricuspid. A pulmonary valve generally has three leaflets.

Pulmonary valve stenosis generally refers to the stenosis of a pulmonary valve or the combination of a pulmonary valve and the right ventricular outflow tract, and it may exist isolatedly or may also be one of the lesions of other complex congenital heart diseases (such as Tetralogy of Fallot). The morbidity from pulmonary stenosis accounts for 10%-20% of the total cases of congenital heart diseases. Depending on different sites of stenosis, pulmonary valve stenosis may be classified as pulmonary valve stenosis, infundibular stenosis, and main pulmonary artery and pulmonary branch stenosis, wherein pulmonary valve stenosis is the most common. The surgical treatments for pulmonary stenosis should be determined according to different lesions, and particularly include (1) pulmonary valve commissurotomy, (2) infundibulum hypertrophic excision, (3) surgical treatment of supravalvular pulmonary stenosis, and (4) surgical repair of pulmonary valve dysgenesis. However, the patches that are used in the above surgical treatments cannot conform to growth of the human body, and easily generate restenosis or valve lesions so that the condition will be increasingly severe with age.

Among right ventricular outflow tract (RVOT) reorganization surgeries for congenital heart diseases, regurgitation of the pulmonary artery is a common postoperative complication and is nearly inevitable. In the last few decades, along with the developments in heart surgery, increasing numbers of patients having complex congenital heart diseases have lived through childhood and survived to adolescence or adulthood, and thus regurgitation of the pulmonary artery has become an increasingly common disease. Originally, regurgitation of the pulmonary artery was considered to be a relatively benign condition, but recently the patho physiology of and the significance of further treatment of pulmonary regurgitation got the attention of cardiovascular physicians. Furthermore, the emerging of pulmonary artery restenosis may probably further aggravate pulmonary regurgitation.

Besides surgical expansion of pulmonary valves/arteries, current transcatheter treatment comprises intervention modes of valve implant or balloon expansion. Transcatheter valve implant only serves as remedy for pulmonary regurgitation from the surgery and requires a secondary procedure, and the balloon expansion may also result in the complication of pulmonary regurgitation. In addition, because the patients of congenital heart diseases are mostly infants and youngsters, prosthetic valves cannot adapt for the growth of the patients, and thus have limited functionality.

Surgery has a remarkable curative effect for treating the patients that undergo RVOT surgery for the first time, but surgery for the second time increases risks of dissociation, hemorrhage and hemostasis, and complications. That is because, although the existing valves can secure themselves to the blood vessel inner wall by the radial supporting force of the stent, most of the positions to secure the stent have undergone surgical treatment, such as the valve annulus was cut during the surgery, so the elasticity and the shape of the blood vessel may no longer be suitable for conventional replacement of a stented valve so that the valve stent is prone to migration.

The existing prosthetic valve implanting techniques also include using a planar (perpendicular to a flow direction through the valve) sewing ring to suture the prosthetic valve to protogenic valve annulus. However, planar sewing rings cannot adapt to new anatomical structures correctly, and have a risk of thrombosis and stenosis.

The prior art that is used to solve the above problems is to conduct redo-surgery or replace the valve by transcatheter delivery. Both of the two methods require another procedure and will certainly cause the complication of pulmonary regurgitation, thereby affecting the function of right ventriculus. If not used for the first time, the transcatheter valve requires another procedure, and the patient may not go to a hospital until the ventriculus dexter dysfunction occurs and at that time the function restoration of ventriculus dexter may be too late.

The PCT patent for invention that has entered the Chinese national phase "PROSTHETIC HEART VALVE" (CN 201180023344.9) discloses a prosthetic valve, comprising an inflow end and an opposing outflow end; a plurality of valve leaflets; a collapsible, self-expandable frame assembly configured to support the valve leaflets and defining a plurality of commissure portions; and a sewing ring portion configured to secure the valve to a surrounding lumen, wherein the plurality of commissure portions are configured to move independently of the sewing ring when the valve is so secured.

In the patent, a self-expandable frame assembly is provided with only one base sewing ring, and thus has a relatively low height, which is inconvenient for being secured into a human heart.

The PCT patent for invention that has entered the Chinese national phase "PROSTHETIC HEART VALVE AND TRANSCATHETER DELIVERED ENDOPROSTHESIS COMPRISING A PROSTHETIC HEART VALVE AND A STENT" (CN 201180036365.4) discloses a prosthetic valve, comprising at least two, preferably three, leaflets, which consist of a natural and/or synthetic material and have a first opened position for opening the heart chamber and a second closed position for closing the heart chamber, the leaflets being able to switch between their first and second position in response to the blood flow through the heart; a leaflet support portion, consisting of biological and/or synthetic material for mounting of the prosthetic heart valve to a stent; and a bendable transition area which forms a junction between the leaflets and the leaflet support portion, the bendable transition area progressing essentially in a U-shaped manner similar to a cusp shape of a natural aortic or pulmonary heart valve for reducing tissue stresses during opening and closing motion of the leaflets.

In the patent, the structure of the stent is complicated, and the suturing structure of the valve leaflets is complicated, both of which result in a high cost for manufacturing the prosthetic valve.

SUMMARY OF THE INVENTION

In view of the problems of the prior art, the present disclosure provides a prosthetic valve wherein the conventional prosthetic valve sewing ring is not present, rather, the valve frame is connected and fixed directly with an anatomical structure of a human body, such as blood vessel wall, through a connecting thread affixed on a frame, thus overcoming the deficiencies associated with prosthetic valve implantation methods of the prior art.

The present disclosure further provides a method for implanting a prosthetic valve by connecting and fixing the prosthetic valve in an implantation position in a human body by use of a connecting thread sutured on the frame of the prosthetic valve. The connecting thread was penetrating through the anatomical structure longitudinally. This overcome the difficulty which exists in the implantation of prosthetic valve in pulmonary position in the prior art.

To achieve the above objectives, the technical solutions of the present disclosure are realized as follows:

the present disclosure provides a prosthetic valve, comprising a tubular frame with a lattice structure that can be radially expanded and deformed and on which a connecting thread is arranged on the frame. While in an implantation position within a human body, the prosthetic valve is connected and fixed to an anatomical structure by use of a connecting thread. The connecting thread forms single or multiple connection that extend radially along the frame. The connection part of the valve frame directly contacts the surrounding anatomical structure.

Optionally, the anatomical structure comprises blood vessel wall.

Optionally, the connecting thread on both sides of the connection part is sutured on the frame after penetrating through the anatomical structure, and the connecting thread knots is located outside the anatomical structure and is in close contact with the anatomical structure.

Optionally, the connecting thread is arranged longitudinally around the frame to form a complete connecting area or to form several sections of interrupted connecting areas.

Optionally, the connecting thread can be distributed at different height in reference to the axis of the frame or at the same height.

Optionally, several U-shaped protrusions are evenly arranged on the frame at a downstream end relative to a blood stream direction; a U-shaped recession is provided between every two adjacent protrusions; one or more foldable joints are provided on edge(s) of each of the recessions such that the protrusions and the recessions are stretched when the prosthetic valve is expanded for implant, and the foldable joints are unfolded when the prosthetic valve is expanded again (for example, by a balloon); the protrusions and the recessions constitute positioning parts of the prosthetic valve leaflets.

Optionally, three protrusions and three recessions are provided on the frame. Three valve leaflets are provided at the protrusions and the recessions, such that the valve leaflets are able to open and close in the blood stream. A covering membrane is provided on the lattice structure of the frame, and the valve leaflets are sutured on the covering membrane such that sutured portions are hermetically engaged to the covering membrane. The suturing thread is optionally sutured on the frame.

Optionally, the protrusions and the recessions are formed by smooth arcuate bending of a same edge.

Optionally, 1-3 foldable joints in the shape of pointed tips are provided, and the tips of the foldable joints point axially to downstream or upstream to the flow of blood.

Optionally, the recession comprises a combination of two smooth arcuate edges, and the arcuate edges are part of the protrusions adjacent to the recessions, and bottom ends of the arcuate edges form part of the lattice structure of the frame.

Optionally, 1-3 foldable joints are provided at each recession wherein at least 1 of the foldable joints is provided between the bottom ends of the two smooth arcuate edges; 1 foldable joint is optionally provided on the smooth arcuate edge.

Optionally, rhombic meshes are provided in the lattice structure of the frame. U-shaped process slots are provided at intersections of net wires to facilitate deformation of the net wires when the tubular frame is radially expanded, and the intersections of the net wires are of an H shape or an X shape.

Optionally, two or more row of the rhombic meshes are provided and are axially distributed along the frame. The mesh array extends downwardly to interior of the protrusions in the blood stream direction.

Optionally, the valve leaflets are sutured along edges of the protrusions and the recessions. Wrinkles of the valve leaflets corresponding to the foldable joints are preserved and can be expanded and deformed when the prosthetic valve is expanded again. And the wrinkles of the covering membrane corresponding to the foldable joints are preserved and can be expanded and deformed when the prosthetic valve is expanded again.

Optionally, the covering membrane is provided on an inner surface, or on an outer surface, or on both of an inner surface and an outer surface, of the lattice structure of the frame.

Optionally, the covering membrane on the outer surface of the lattice structure of the frame comprises an upper covering membrane and a lower covering membrane, the upper covering membrane wraps the protrusions and part of a frame body, the lower covering membrane wraps the remaining part of the frame. The upper covering membrane and the lower covering membrane are made of different materials or the same material and are sutured together along a periphery of the frame.

Optionally, the frame and the protrusions are manufactured integrally by laser cutting, wire braiding/weaving or 3D printing.

Optionally, the frame and its protrusions are compressed into a slim tubular shape before the prosthetic valve is radially expanded and distorted by a force being applied from the interior of the slim tube. The frame and its protrusions are manufactured by using a shape memory functional material to realize self-expansion.

Optionally, a guide loop is provided on an arch portion of each protrusion, wherein the guide loop is formed at the arch portion of the protrusion; or several U-shaped or V-shaped guides on the frame are provided at an upstream end relative to the blood stream direction. The guides extend out of the frame, and the guides and the frame are manufactured integrally.

Optionally, a U-shaped or V-shaped reinforcement is connected to two edges of a corresponding recession.

The protruding direction of the reinforcements is the same as the arch direction of the protrusions, and the two bottom ends of each reinforcement are respectively connected to the two edges of the corresponding recession.

Optionally, a guide loop is provided on the protruding portion of each reinforcement, and the annular guide is formed by bending an edge at the protruding portion of the reinforcement.

Optionally, the prosthetic valve frame is expandable during the implantation into the heart, and the prosthetic valve can be expended again later time after implant.

The present disclosure further provides a method for implanting a prosthetic valve, in which the method comprises the following steps:

(1) a prosthetic valve is placed in an intended position within a human body for long term implantation;

(2) connecting threads are provided between the anatomical structure of human body and the frame on the prosthetic valve at implantation position;

Optionally, the connecting thread on both sides of the connection part is sutured on the frame after penetrating through the anatomical structure longitudinally, the connecting thread external of the connection part locates outside of the anatomical structure, is in close contact with the anatomical structure.

The prosthetic valve of the present disclosure has the following advantages:

The prosthetic valve of the present disclosure is suitable for surgical implantation, and, by open heart surgery, is secured to the anatomical structure by connecting thread.

The prosthetic valve of the present disclosure does not have a horizontal suturing ring (parallel to the valve annulus plane) to adapt to the physiological anatomical conditions of corresponding valve positions. It has the advantages of stable implantation, and is specifically suitable for patients who need certain valve replacement surgery, such as patient with pulmonary stenosis.

The prosthetic valve of the present disclosure can be expanded multiple times to adapt for the growth of the patient, which avoids the future surgical procedures in the prior art that requires replacement of the prosthetic valve and alleviates complication from redo surgery.

The prosthetic valve of the present disclosure is suitable to serve as a replacement of the pulmonary valve.

Compared with the prior art, the prosthetic valve of the present disclosure has the characteristics of a simple structure and low manufacturing cost.

Figure 1:
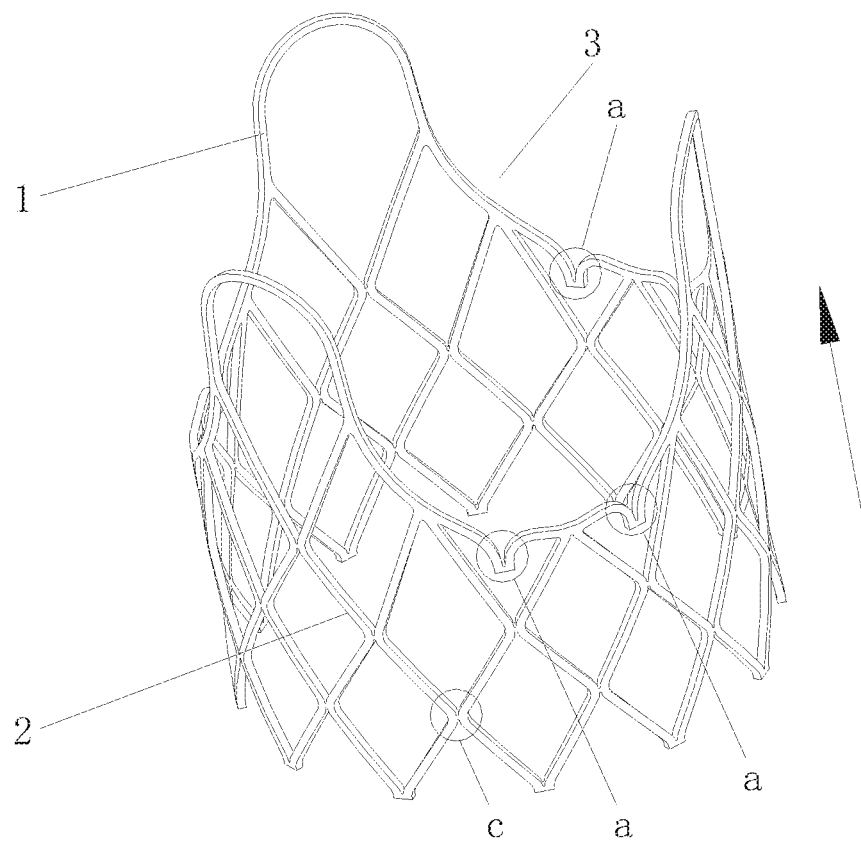
FIG. 1 is a perspective view of the stent that is employed by the prosthetic valve of Embodiment 1 of the present disclosure.

In the drawings: 1. protrusions; 2. frame; 3. recessions; 4. inner covering membrane; 4-1. suturing edge; 5. outer covering membrane; 5-1. suturing edge; 5-2. suturing edge; 5-3. lower covering membrane; 5-4. upper covering membrane; 6. valve leaflets; 7. guides; 8. reinforcements; 9. blood vessel; 10. connecting thread. A. foldable joint; B. foldable joint; C. X-shaped connection; D. H-shaped connection.

DETAILED DESCRIPTION

In order to make the purposes, the technical solutions and the advantages of the present disclosure clearer, the embodiments of the present disclosure will be described below in further detail in conjunction with the drawings.

Embodiment 1

FIG. 1 shows one of the embodiments of the present disclosure. In the present embodiment, a prosthetic valve comprises a tubular frame 2; frame 2 has a lattice structure that can be radially expanded and distorted.

Figure 10:
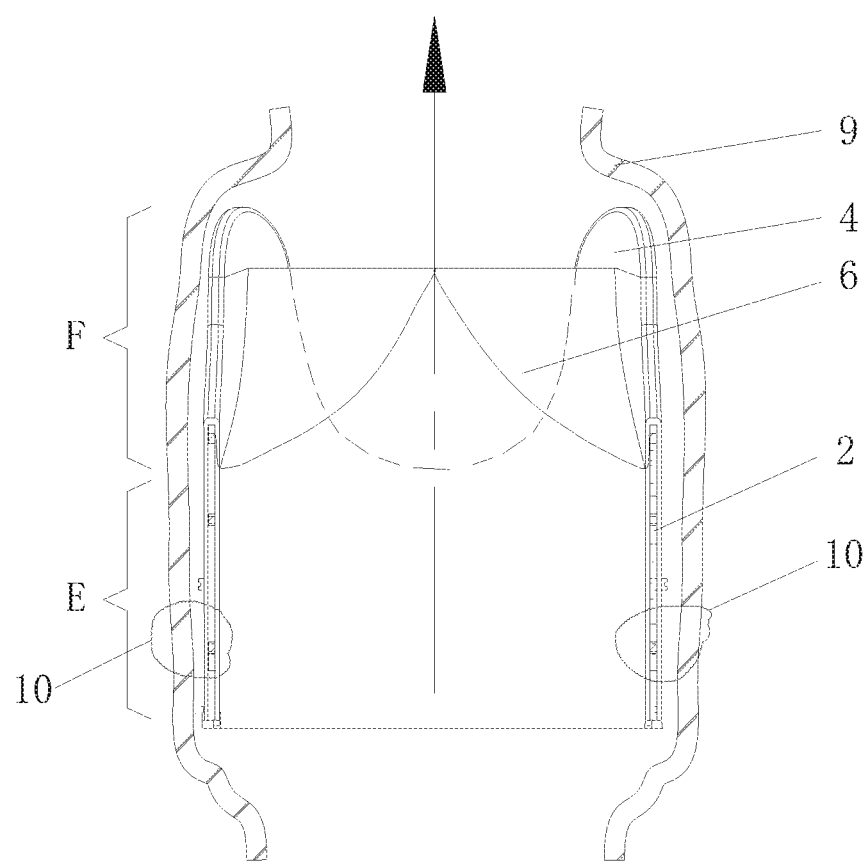
FIG. 10 is the sectional view along the line A-A of FIG. 9.
Figure 11:
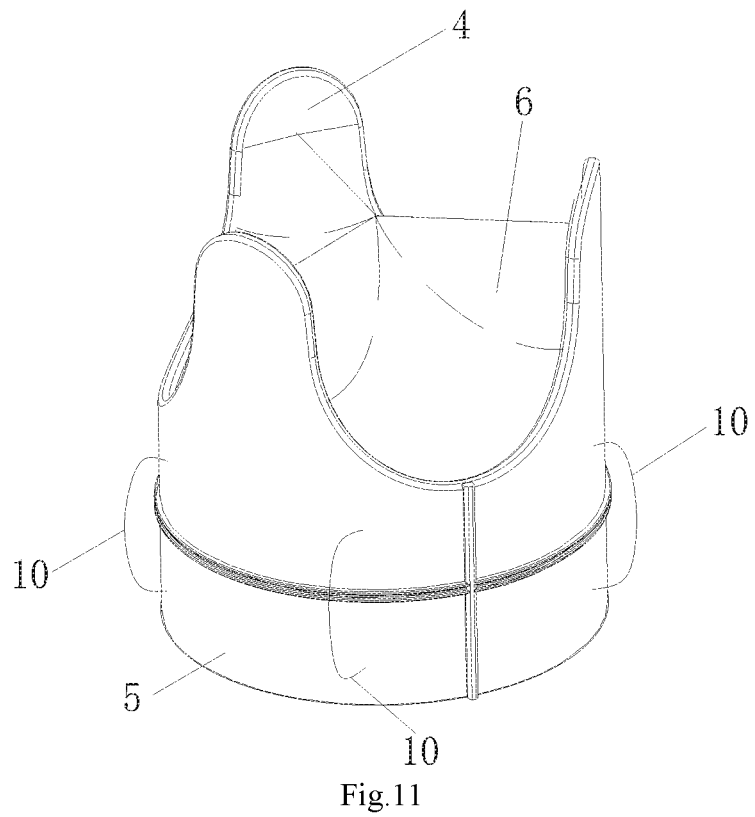
FIG. 11 shows the schematic view of the structure of connecting thread of a prosthetic valve of the present disclosure; the connecting thread is shown as distributed up and down.
Figure 12:
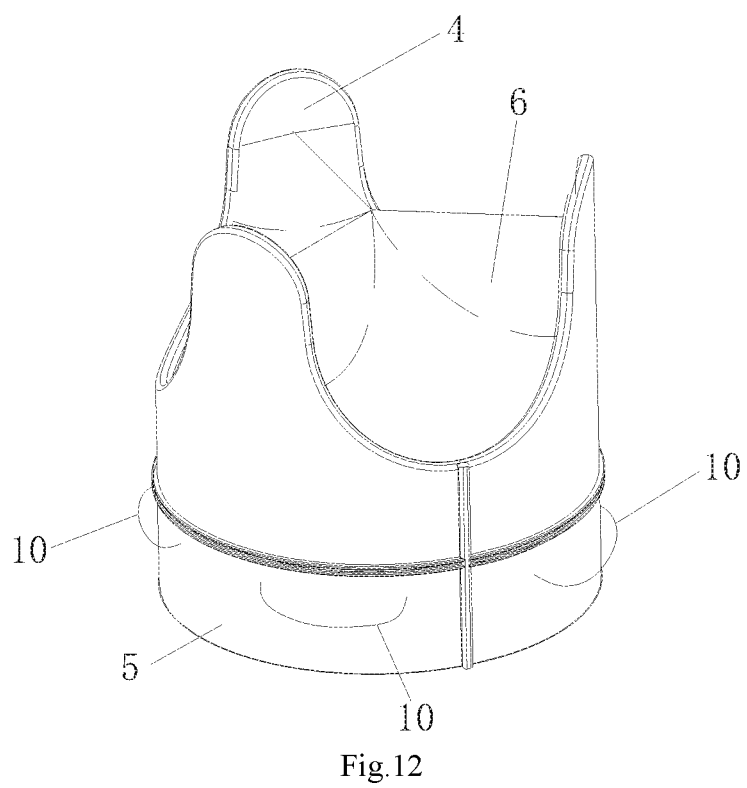
FIG. 12 shows the schematic view of the structure of connecting thread of a prosthetic valve of the present disclosure; the connecting thread is shown as distributed horizontally.

As shown in FIG. 10, a connecting thread 10 is arranged on frame 2, the prosthetic valve in an implantation position is connected and fixed with an anatomical structure of a human body, such as blood vessel wall, by a connecting thread. The connecting thread 10 forms a plurality of connection portions around the frame 2, as shown in FIG. 11 and FIG. 12 wherein the connection portions extend radially along the frame 2. The connection portions are in close contact with the anatomical structure. The connection is similar to a U-shape or V-shape.

As shown in FIG. 10, the connecting thread on both sides of the connection part, whose direction is approximately the circumferential direction of the blood vessel wall, is sutured on the frame after penetrating through the anatomical structure longitudinally, and the connecting thread knots are located outside the anatomical structure and is in close contact with the anatomical structure.

The connecting thread is arranged around the periphery of the frame 2. When using a long connecting thread, it could form a complete circle of connecting areas. When using several short connecting threads, they will form several sections of interrupted connecting areas. FIG. 11 and FIG. 12 shows several sections of interrupted connecting areas.

As shown by FIG. 11, the connecting thread on both sides of the connection part is distributed up and down along the axial direction of the frame 2. As shown by FIG. 12, the connecting thread on both sides of the connection part is crossing frame and the anatomical structure along the periphery of the frame. FIG. 10 shows the state where the connecting thread is distributed up and down along the axial direction of the frame 2.

The suturing of the connecting thread 10 is different from the existing suturing method in the prior art. It does not have a horizontal suturing ring, has the advantages of stable implantation, is not prone to displacement and migration, and is also suitable for patients with pulmonary stenosis.

The structure of the connecting thread described above merely provides a practical connection and fixation structure for a product such as a prosthetic valve. The technical solution is not for the purpose of treating a certain type of diseases. It does not belong to a process for identifying, determining or eliminating the cause of a lesion, but rather is a method of use for a device treating a disease. For the convenience of description, it is inevitable to mention the blood vessel and the blood vessel wall at the implantation position within the human body, but this is not an improvement to the surgical method; It is only for defining the structural characteristics of connecting thread in relationship to a device and the surrounding anatomical structure.

Three U-shaped protrusions 1 on the frame 2 are evenly arranged at the downstream end relative to blood stream direction. U-shaped recession 3 is provided between every two adjacent protrusions 1. Several foldable joints are provided on each edge of the recessions 3, such as the foldable joints A shown in FIG. 1. The protrusions 1 and the recessions 3 are stretched when the prosthetic valve frame is expanded during implant, and the foldable joints A are unfolded when the prosthetic valve is expanded after implant.

The blood stream direction is indicated by the arrow in FIG. 1. The numbers of the protrusions 1 and the recessions 3 are preferably three, and the numbers may be increased according to design requirements, for example, increased to six or nine.

As shown in FIG. 10, part E of the frame 2 is a part where the connecting thread 10 is provided, part F constitutes a positioning part when the prosthetic valve is connected to the blood vessel wall, that is, during implant, it is possible to determine the connecting position by sensing the protrusion 1 and the recession 3 on the frame 2 from outside of blood vessel wall 9.

The purpose of providing the foldable joints A is to provide for future expansion in addition to the expansion of the prosthetic valve frame during implant. When the prosthetic valve is expanded during implant, the foldable joints A are still in the folded state, or are unfolded at a smaller scale. In the subsequent stage after the implant, as the patient grows, the prosthetic valve may be further expanded, so as to adapt for the growth of the patient's heart. Further expansion may be once or several times, but generally does not exceed twice.

Because the structures of the protrusions 1 and the recessions 3 on the frame 2 are all U-shaped, which has a wide bottom edge, the protrusions 1 and the recessions 3 cannot be stretched more easily than the foldable joints A; the U shape structure is substantially different from the V-shaped protrusions and recessions that are commonly used in the prior art. If the protrusions 1 and the recessions 3 are V-shaped, the side edges of the protrusions and the recessions will, in the extending process, expand together with the small foldable joints, which would make the valve leaflet dysfunctional.

Figure 3:
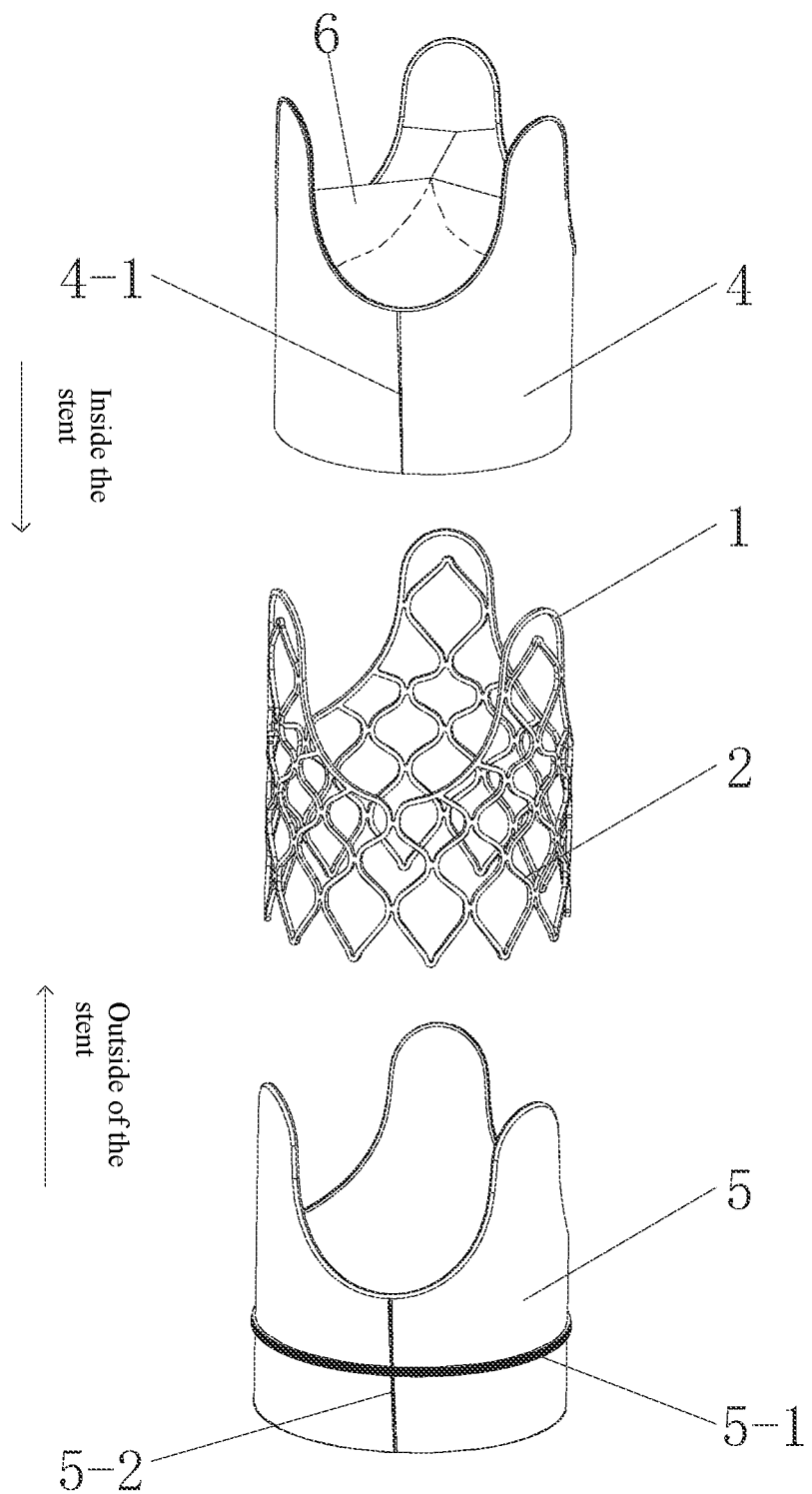
FIG. 3 is the exploded view of a prosthetic valve of the present disclosure.
Figure 8:
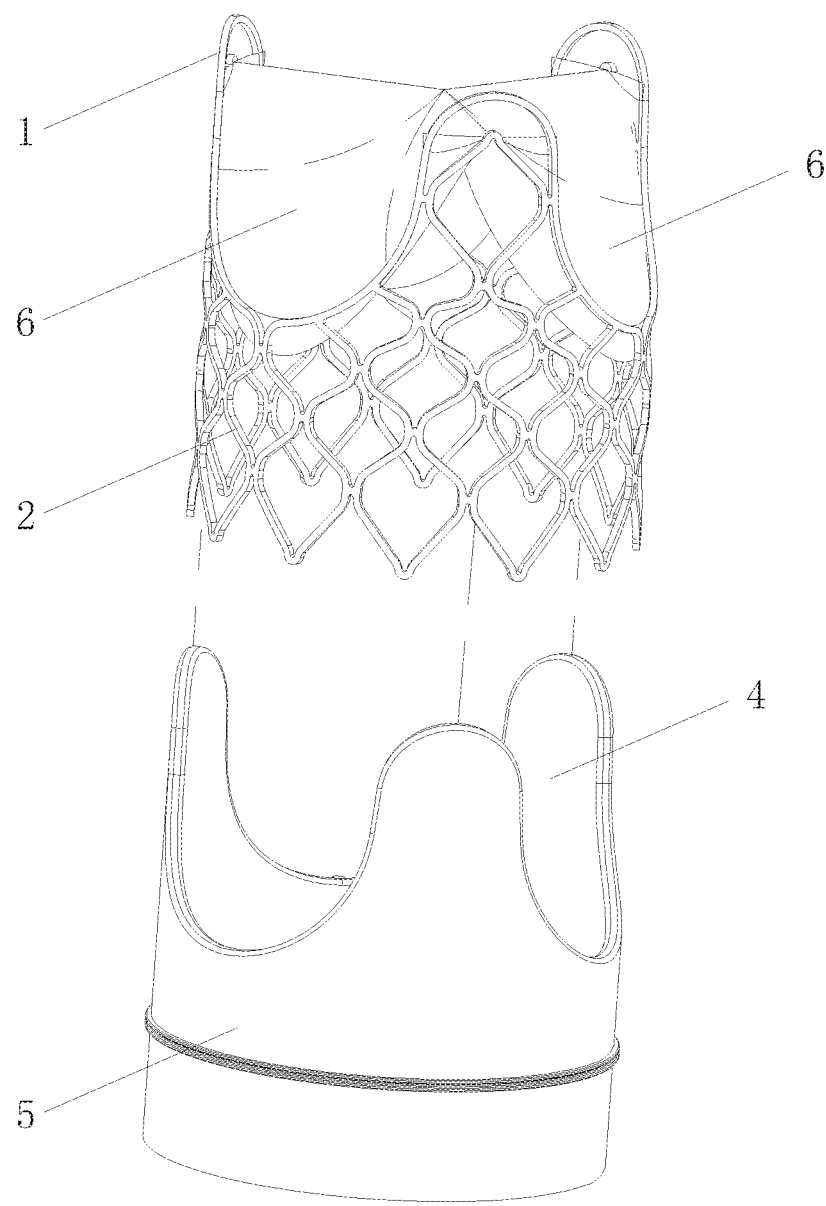
FIG. 8 is a diagram of the position relationship between the stent and the valve leaflets that are employed by the prosthetic valve of the present disclosure.
Figure 9:
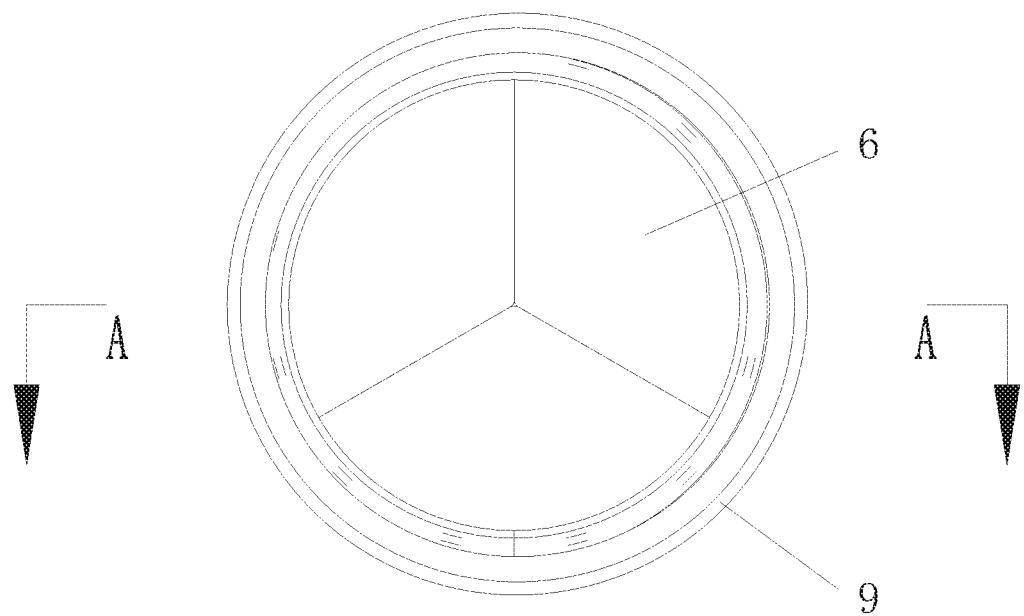
FIG. 9 is the bottom view of the prosthetic valve of the present disclosure after having been implanted into the pulmonary artery.

As shown by FIGS. 3 and 8, three valve leaflets 6 are provided at the protrusions 1 and the recessions 3 so that the valve leaflets 6 are able to open and close in the blood stream. A covering membrane is provided on the lattice structure of the frame 2. The valve leaflets 6 are sutured on the covering membrane, with sutured portions hermetically engaged to the covering membrane. If the valve leaflets 6 are directly sutured on the stent, each of the suturing points forms a stress concentration whereas if they are sutured on the covering membrane, the stresses are more evenly distributed, improving hemodynamics and durability of the valve leaflets 6. The suturing thread may optionally be sutured through the frame 2.

The valve leaflets 6 may be designed with various shapes, such as half-moon shape, elliptical shape, U shape or approximately egg shape. The material of the valve leaflets 6 may employ animal (preferably porcine) valves, porcine or bovine pericardium materials, biological tissue materials, polymer materials or tissue engineering materials.

As shown by FIG. 1, the protrusions 1 and the recessions 3 are formed by the smooth arcuate bending of a same edge.

In the present embodiment, 1-3 foldable joints A in a shape of pointed tips are provided, and the tips of the foldable joints A point axially to downstream or upstream of blood stream direction. When the prosthetic valve is expanded after implant, the foldable joints A may be unfolded to become a smooth curve.

Rhombic meshes are provided in the lattice structure of the frame 2. U-shaped slots are provided at intersections of net wires to facilitate deformation of the net wires when the tubular frame is radially expanded, and the intersections of the net wires are of an H shape or an X shape, such as the X-shaped connection C shown in FIG. 1.

As shown by FIG. 1, at least an upper layer and a lower layer of the rhombic meshes are axially distributed along the frame, and the mesh array stack up to protrusion in the blood stream direction to converge in the interior of the three U-shaped protrusions 1. This structure facilitates enhancing the structural strength of the protrusions 1 and improving the elasticity of the protrusions 1.

The valve leaflets 6 are sutured along edges of the protrusions 1 and the recessions 3, wrinkles corresponding to the foldable joints A on the valve leaflets are preserved, and can be expanded and deformed when the prosthetic valve is expanded after implant. The design of the wrinkles is to provide seal after the expansion.

Wrinkles of the covering membrane corresponding to the foldable joints A are also preserved, and can be expanded and deformed when the prosthetic valve is expanded after implant. The design of the wrinkles is to prevent perivalvular leak.

Figure 4:
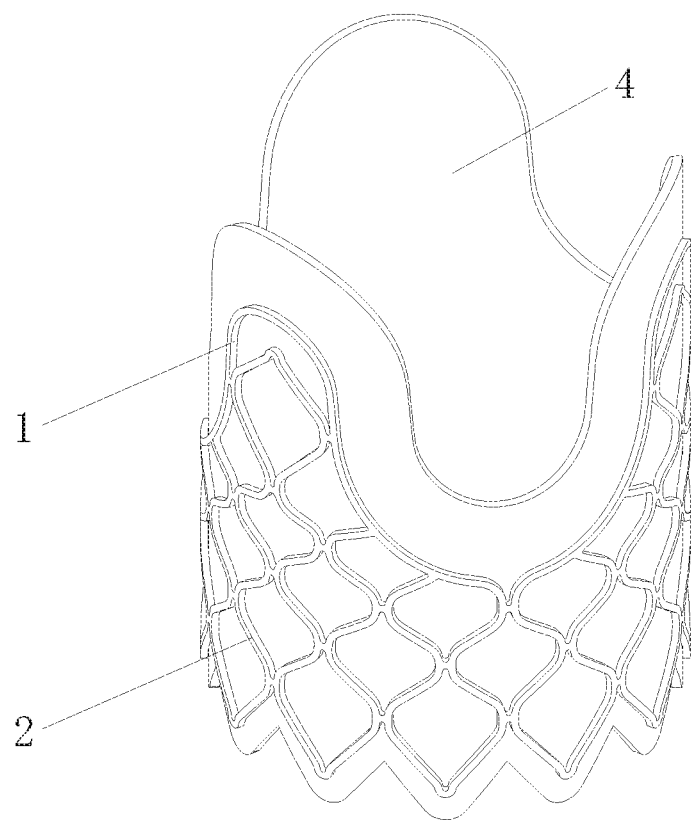
FIG. 4 is the assembly view of the inner covering membrane and the stent that are employed by the prosthetic valve of the present disclosure.
Figure 5:
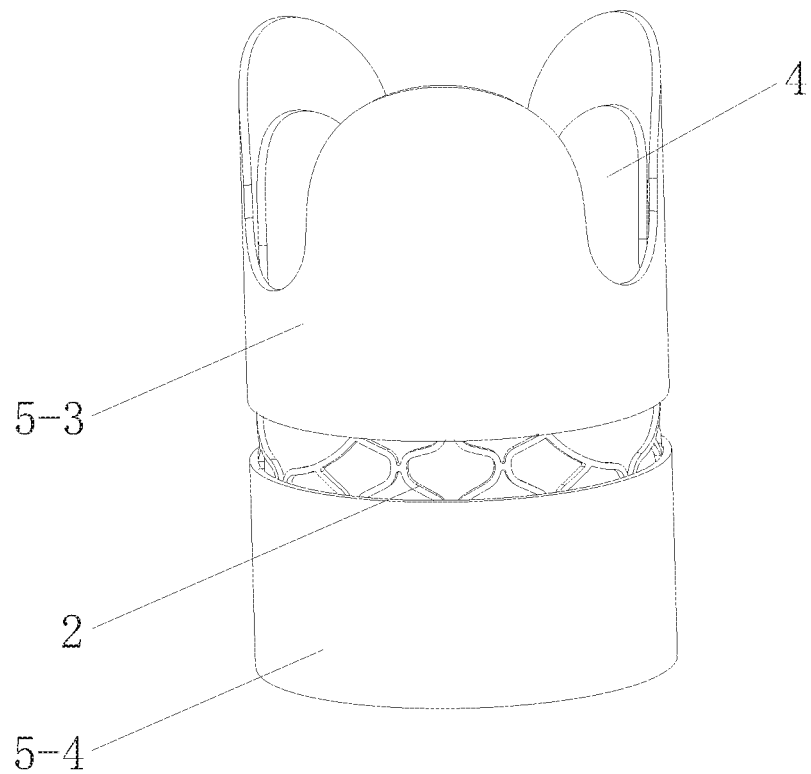
FIG. 5 is the assembly view of the inner covering membrane, the outer covering membrane and the stent that are employed by the prosthetic valve of the present disclosure.
Figure 6:
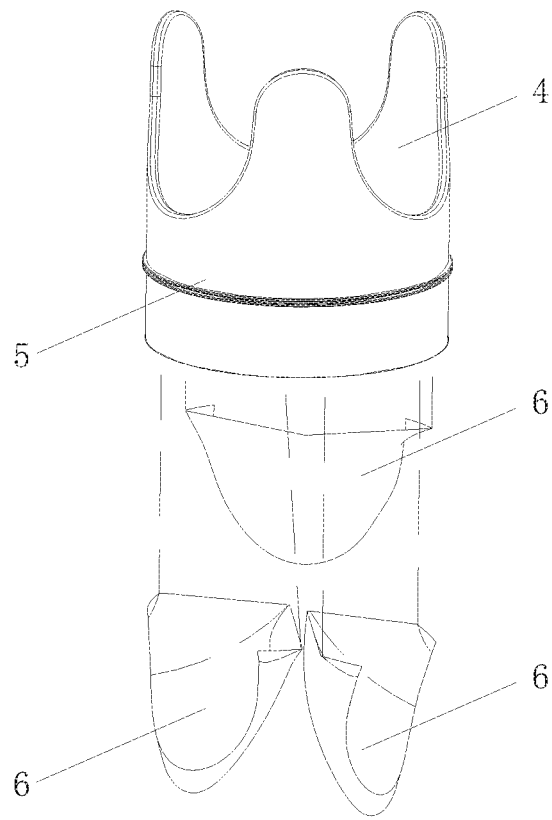
FIG. 6 is the assembly view of the covering membrane and the valve leaflets that are employed by the prosthetic valve of the present disclosure.
Figure 7:
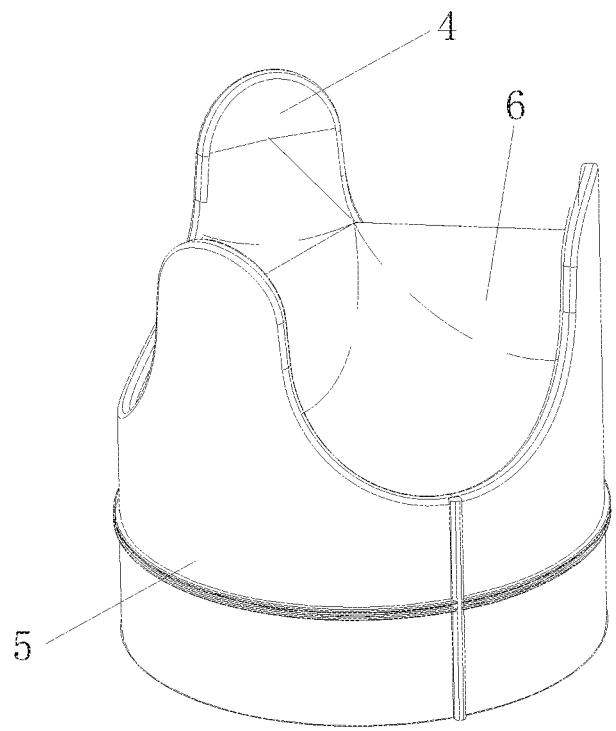
FIG. 7 is the perspective view of the prosthetic valve of the present disclosure.

As shown by FIGS. 3, 4 and 5, covering membranes are provided on both of the inner surface and the outer surface of the lattice structure of the frame 2, that is, the inner covering membrane 4 and the outer covering membrane 5 in the figures. The inner covering membrane 4 and the outer covering membrane 5 are required to be sutured together at the upstream end and downstream end relative to the blood stream direction.

The inner covering membrane 4 will be joined at the suturing edge 4-1.

The outer covering membrane 5 on the outer surface comprises an upper covering membrane and a lower covering membrane, the upper covering membrane 5-3 wraps the three protrusions 1 and part of the frame body of the frame 2; the lower covering membrane 5-4 wraps the remaining part of the frame body of the frame 2. The upper and the lower covering membrane can be manufactured from different materials or the same material. They are firstly individually joined along the suturing edge 5-2, and then sutured together along the periphery of the frame 2 (the suturing edge 5-1). The upper covering membrane 5-3 is manufactured from pericardium materials, such as porcine or cattle pericardium material, which have the characteristics of a smooth surface and is resistant to thrombus formation. The material of the lower covering membrane 5-4 is not specially limited, and it may employ the material the same as that of the upper covering membrane 5-3.

The frame 2 and the three U-shaped protrusions 1 are manufactured integrally, and are manufactured by laser cutting, wire braiding/weaving or 3D printing. The frame 2 and the three U-shaped protrusions 1 are optionally manufactured by using elastic alloy materials, and may also be manufactured by using shape memory alloy materials, such as nickel titanium alloy.

The frame 2 and the three U-shaped protrusions 1 were compressed into a slim tube shape before the prosthetic valve is radially expanded and deformed, and a force is balloon-expansion force applied from the interior of the tube shape to make the frame 2 and the three U-shaped protrusions 1 expand and deform. The implanting method and the implanting instruments may refer to the medical procedures in the prior art.

If the frame 2 and the three U-shaped protrusions 1 are made of a shape memory alloy material, the frame 2 and the three U-shaped protrusions 1 may self-expand.

If the prosthetic valve is implanted surgically, the prosthetic valve may be conformed to a suitable size before implant. If the prosthetic valve is implanted by transcatheter delivering and the prosthetic valve is expanded to a suitable size after it has been delivered to the positions of the pulmonary valve.

In order to facilitate transcatheter implant, a guide loop may be provided on the arch portion of each protrusion 1. The guides may be connected to the leading wire that is used in the implantation procedure, and the guide is formed by the bent edge at the arch portion of the protrusion 1. A representative structure is shown in FIG. 11.

The prosthetic valve is expanded for the first time during the implantation into a human body (which applies to other animal bodies), and the prosthetic valve can be expanded again a period of time after initial implant is completed. The size at initial implant and subsequent expanded sizes is to fit the structures of corresponding anatomical structure of the patient (the pulmonary artery, for example).

Embodiment 2

Figure 2:
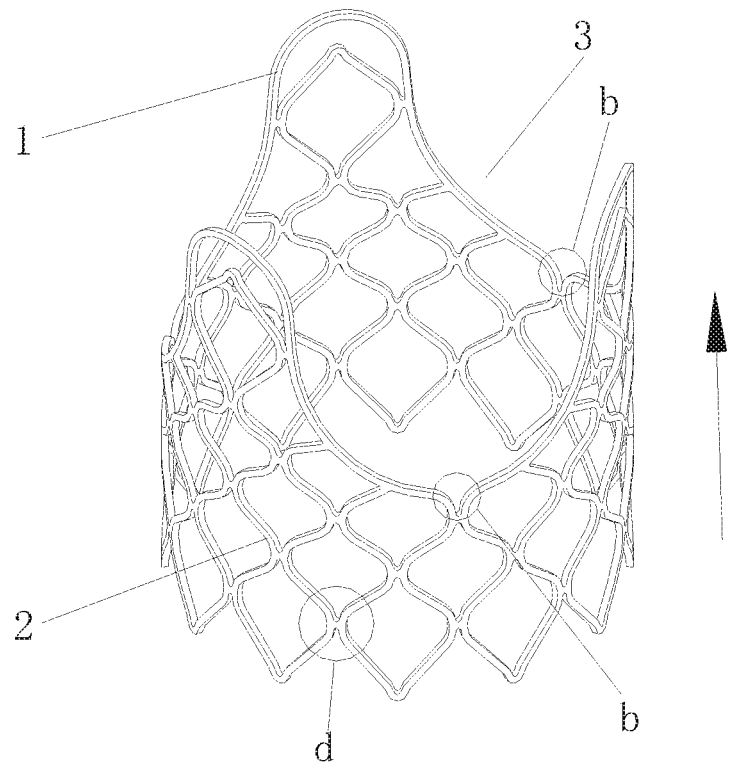
FIG. 2 is a perspective view of the stent that is employed by the prosthetic valve of Embodiment 2 of the present disclosure.

FIG. 2 shows Embodiment 2 of the present disclosure. In the present embodiment, what is different from Embodiment 1 is that all of the protrusions 1 and the recessions 3 are U-shaped, the recessions 3 comprise a combination of two smooth arcuate edges, the two arcuate edges are individually part of the protrusions 1 adjacent to the recessions, and the bottom ends of the two arcuate edges are connected to the lattice structure of the frame 2.

In the present embodiment, 1-3 foldable joints B are provided wherein at least 1 foldable joint B is provided between the bottom ends of the two smooth arcuate edges. When the prosthetic valve is expanded during implant, the foldable joints B are still in the folded state, and the foldable joints B are unfolded when the prosthetic valve is expanded after implant.

When the prosthetic valve is expanded again, the foldable joints B cannot be unfolded to be a smooth curve, but the foldable joints B have simpler structure and can be manufactured more easily than the foldable joints A.

Optionally, the smooth arcuate edges may be provided with 1 additional foldable joint, and the foldable joints on those positions may refer to the structure of the foldable joints A.

In the present embodiment, approximately rhombic meshes are provided in the lattice structure of the frame 2. U-shaped process slots are provided at intersections of the net wires, to facilitate deformation of the mesh when the tubular frame is radially expanded, and the intersections of the mesh are of an H shape or an X shape, such as the H-shaped connection D shown in FIG. 2.

The other structures of the prosthetic valve of the present embodiment are the same as those of Embodiment 1 and will not be described in detail here.

Embodiment 3

Figure 13:
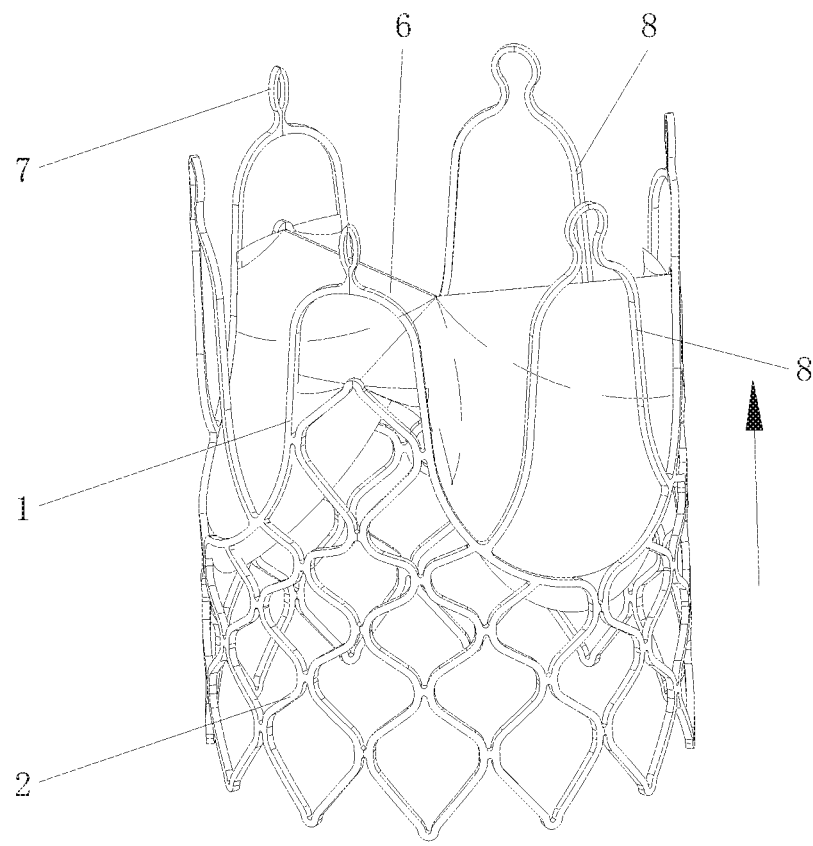
FIG. 13 shows the perspective view of the stent that is employed by the prosthetic valve of Embodiment 3 of the present disclosure (the figure shows the valve leaflets).

FIG. 13 shows Embodiment 3 of the present disclosure. In the present embodiment, what is different from Embodiment 1 is that U-shaped reinforcement 8 is connected to two edges of the corresponding recession 3, the protruding direction of the reinforcements 8 is the same as the arch direction of the protrusions 1, and the two bottom ends of the reinforcement 8 are respectively connected to the two edges of the corresponding recession 3. The reinforcements 8 can enhance the structural strength of the protrusions 1 and improve their elasticity.

Guide loop 7 is provided on the protruding portion of each reinforcement 8, and the guide 7 is formed by the bending edge at the protruding portion of the reinforcement.

The guides 7 may be connected to the leading wire that is used in the implantation procedure in order to adjust the implantation position of the prosthetic valve.

The frame 2, the three U-shaped protrusions 1 and the reinforcements 8 are manufactured integrally. The reinforcements 8 may also be V-shaped.

The other structures of the prosthetic valve of the present embodiment are the same as those of Embodiment 1 and will not be described in detail here.

Embodiment 4

Figure 14:
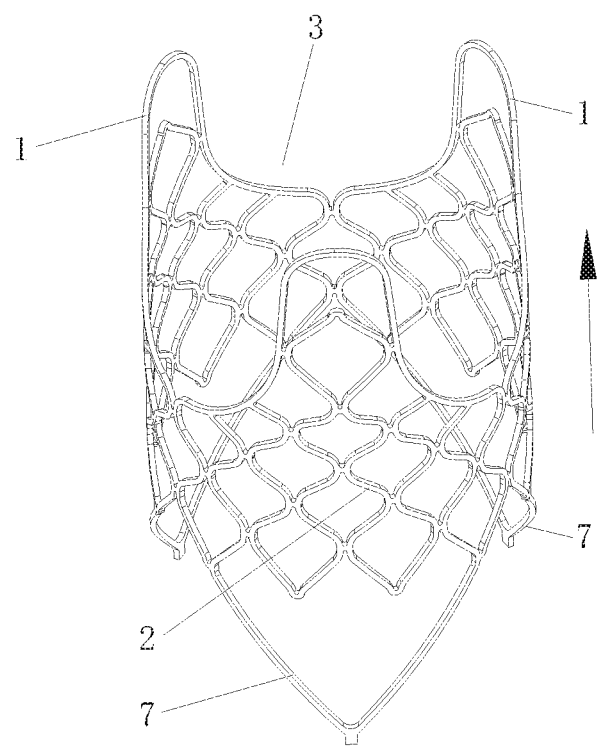
FIG. 14 shows the perspective view of the stent that is employed by the prosthetic valve of Embodiment 4 of the present disclosure.

FIG. 14 shows Embodiment 4 of the present disclosure. In the present embodiment, what is different from Embodiment 1 is that several V-shaped guides 7 are provided at the upstream end of the frame 2 relative to the blood stream direction, the guides 7 extend out of the frame 2, and the guide 7 and the frame 2 are manufactured integrally.

The width of the guides 7 and the width of the mesh of the frame 2 may be the same.

The guides 7 may also be set to be U-shaped.

The guides 7 may be connected to the leading wire that is used in the implantation procedure to adjust the implantation position of the prosthetic valve in the heart and is for retraction of the valve.

The other structures of the prosthetic valve of the present embodiment are the same as those of Embodiment 1 and will not be described in detail here.

Embodiment 5

In the present embodiment, the present disclosure provides a method for implanting a prosthetic valve, specifically provides a method of implanting the prosthetic valve according to Embodiments 1-4 into human body, for example, when implanting the prosthetic valve into pulmonary position. This method may also serve as a reference for a prosthetic valve to be implanted to other positions.

The method comprises the following steps:
(1) a prosthetic valve is placed to the position of pulmonary valve through either open heart surgery or catheter;
(2) a connecting thread is provided between the blood vessel wall of pulmonary artery and the frame of the prosthetic valve;
(3) the connecting thread is sutured on the frame after penetrating through the blood vessel wall longitudinally, the prosthetic valve is sutured to the blood vessel wall of the pulmonary artery by connecting thread, the connecting thread forms a plurality of connection portions around the periphery of the frame with the connection portions distributed along the frame, and is in close contact with the blood vessel wall.

Surgical instruments in the prior art may be used for suturing the valve, which is not described in detail herein.

The connecting thread on both sides of the connection part is sutured on the frame after penetrating through the pulmonary artery longitudinally, and the connecting thread knots outside the connection part is located outside the pulmonary artery, and is in close contact with the vessel wall.

In the present invention, the covering membrane on the outer surface of the mesh structure of the frame comprises an upper covering membrane and a lower covering membrane, the upper covering membrane wraps the protrusions and part of a frame body, the lower covering membrane wraps the remaining part of the frame, the upper covering membrane and the lower covering membrane are made of different materials or the same material, and are sutured together along a periphery of the frame. The lower cover membranes of inner and/or outer frame surface are in the range of 2-15 mm in height.

In the present invention, the connecting thread on both sides of the connection portion is sutured on the frame after penetrating through the anatomical structure vertically, and the connecting thread outside the connection portion is located outside of the anatomical structure, is in close contact with the anatomical structure. The connecting thread does not need to go through a horizontal suturing ring (parallel to the valve annulus plane) to adapt to the physiological anatomical conditions of corresponding valve positions; but go through lower covering membrane and the anatomical structure.

The above descriptions are merely preferable embodiments of the present disclosure and do not limit the scope of the present disclosure. Any modifications, equivalent substitutions or improvements that are made within the spirit and principle of the present disclosure are all included in the scope of the present disclosure.

The invention claimed is:

1. A prosthetic valve, comprising:
a tubular frame being a mesh structure, radially expandable and deformable,
wherein the tubular frame is provided with a connecting thread,
the connecting thread is configured to fixedly connect the tubular frame with an anatomical structure in an implantation position within a human body,
the connecting thread forms multiple connection portions, each connection portion passes through the tubular frame and along an inner surface of the tubular frame that extends radially along the tubular frame, space surrounded by the connecting portions are configured to accommodate a thickness of the anatomical structure, the multiple connection portions of a prosthetic valve frame are configured to directly contact the surrounding anatomical structure;
U-shaped protrusions are evenly arranged on the tubular frame at a downstream end with respect to a blood stream direction;
a U-shaped recession is provided between every two adjacent U-shaped protrusions;
one or more foldable joints are provided on edge(s) of each of the recessions such that the protrusions and the recessions are configured to unfold when the prosthetic valve is first expanded at the implantation position, and the foldable joints are configured to unfold when the prosthetic valve is expanded again; the protrusions and the recessions constitute a positioning anchor when the prosthetic valve is connected to the anatomical structure;
wherein three protrusions and three recessions are provided, three valve leaflets are provided at the protrusions and the recessions, and the valve leaflets are configured to open and close in a blood stream; a covering membrane is provided on the mesh structure of the tubular frame, and the valve leaflets are sutured on the covering membrane such that sutured portions are hermetically engaged to the covering membrane, and suturing thread does or does not pass through pass the tubular frame;
said covering membrane is provided on an outer surface of the mesh structure or on both of the inner surface of the tubular frame and the outer surface of the mesh structure; and
wherein the covering membrane on the outer surface of the mesh structure comprises an upper covering membrane and a lower covering membrane, the upper covering membrane wraps the protrusions and part of a tubular frame, the lower covering membrane wraps the remaining part of the tubular frame, the upper covering membrane and the lower covering membrane are made of different materials or the same material, and are sutured together along a periphery of the tubular frame.

2. The prosthetic valve according to claim 1, wherein the anatomical structure comprises a blood vessel wall.

3. The prosthetic valve according to claim 1, wherein
The connecting thread forming each connection portion passes through the tubular frame and along the inner surface of the tubular frame.

4. The prosthetic valve according to claim 1, wherein the connecting thread is arranged longitudinally around the tubular frame to form a completely connected regions or to form a plurality of discretely connected regions.

5. The prosthetic valve according to claim 1, wherein the connecting thread forming each connection portion is vertically oriented along an axial direction of the tubular frame or horizontally oriented along the outer surface of the mesh structure, distributed at different heights in reference to the axial direction of the tubular frame or at the same height.

6. The prosthetic valve according to claim 1, wherein the protrusions and the recessions are formed by one integral edge with smooth curves.

7. The prosthetic valve according to claim 6, wherein 1-3 foldable joints in the shape of pointed tips are provided, and the tips of the foldable joints point to a direction axially or upward along the mesh frame, to downstream or upstream to a blood flow.

8. The prosthetic valve according to claim 6, wherein a U-shaped or V-shaped reinforcement is connected to two edges of a corresponding recession, a protruding direction of the reinforcements is the same as an arch direction of the protrusions, and two bottom ends of each reinforcement are respectively connected to the two edges of the corresponding recession.

9. The prosthetic valve according to claim 1, wherein each recession is made of two smooth arcuate edges, and the two arcuate edges are respectively a part of the adjacent protrusions on both sides, and a bottom edge of the recessions form part of the mesh structure of the tubular frame.

10. The prosthetic valve according to claim 1, wherein
1-3 foldable joints are provided at each recession wherein
at least 1 of the foldable joints is provided between bottom ends of two smooth arcuate edges; and
1 foldable joint is either provided on each smooth arcuate edge or not.

11. The prosthetic valve according to claim 1, wherein rhombic meshes are provided in the mesh structure of the tubular frame, U-shaped process slots are provided at intersections of mesh lines, to facilitate distortion of the mesh lines when the tubular frame is radially expanded, and the intersections of the mesh lines are H-shaped or X-shaped.

12. The prosthetic valve according to claim 1, wherein the valve leaflets are sutured onto the corresponding edges of the protrusions and the recessions, wrinkles of the valve leaflets with respect to the foldable joints are preset and configured to be expanded and deformed as the prosthetic valve is expanded; and wrinkles of the covering membrane corresponding to the foldable joints are preset and configured to be expanded and deformed as the prosthetic valve is expanded.

13. The prosthetic valve according to claim 1, wherein a guide loop is provided on an arch portion of each protrusion, wherein the guide loop is formed by bending an edge of the arch portion of the protrusions; or several U-shaped or V-shaped guide loops on the tubular frame are provided at an upstream end with respect to the blood stream direction, the guide loops extend out of the tubular frame, and the guide loops and the tubular frame are manufactured integrally.

14. The prosthetic valve according to claim 1, wherein
The prosthetic valve is configured to be first expanded at the implantation position during implantation into the heart, and
the prosthetic valve is configured to be expanded again at a later time after implantation.

* * * * *